United States Patent
Beeckler

(10) Patent No.: US 12,364,538 B2
(45) Date of Patent: Jul. 22, 2025

(54) INDIFFERENT ELECTRODE WITH SELECTABLE AREA

(71) Applicant: Biosense Webster (Israel) Ltd., Yokneam (IL)

(72) Inventor: Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 526 days.

(21) Appl. No.: 16/180,357

(22) Filed: Nov. 5, 2018

(65) Prior Publication Data

US 2020/0138513 A1     May 7, 2020

(51) Int. Cl.
*A61B 18/16*     (2006.01)
*A61B 18/12*     (2006.01)
(Continued)

(52) U.S. Cl.
CPC .......... *A61B 18/16* (2013.01); *A61B 18/1206* (2013.01); *A61B 18/1492* (2013.01);
(Continued)

(58) Field of Classification Search
CPC ................ A61B 18/16; A61B 18/1206; A61B 18/1492; A61B 2018/00351;
(Continued)

(56) References Cited

U.S. PATENT DOCUMENTS 3,662,745 A * 5/1972 Cosentino ............... A61L 2/035
204/418
6,007,532 A * 12/1999 Netherly ............... A61N 1/0492
606/35
(Continued)

FOREIGN PATENT DOCUMENTS

EP     1847230 A1    10/2007
EP     2022427 A1    2/2009
JP    2008-253777 A   10/2008

OTHER PUBLICATIONS

Extended European Search Report dated May 15, 2020 from related EP 19206945.8.
(Continued)

*Primary Examiner* — Daniel W Fowler
*Assistant Examiner* — Lindsay Regan Lancaster
(74) *Attorney, Agent, or Firm* — Clayton, McKay & Bailey, PC

(57) ABSTRACT

A system includes an indifferent electrode, electrical switching circuitry, and a processor. The indifferent electrode, which is configured for placement on a body of a patient, includes multiple electrically-conducting sub-electrodes that are electrically-insulated from one another. The electrical switching circuitry is configured to receive a control signal that specifies a selected subset of the sub-electrodes, and in response to electrically connect the selected subset, so as to close an electrical circuit passing through the body of the patient. The processor is configured to determine a required surface area of the indifferent electrode, select the subset of the sub-electrodes that together have the required surface area, and instruct the electrical switching circuitry to electrically connect the selected subset of the sub-electrodes.

11 Claims, 2 Drawing Sheets

(51) Int. Cl.
    *A61B 18/14*      (2006.01)
    *A61B 18/00*      (2006.01)
(52) U.S. Cl.
    CPC ........... *A61B 2018/00351* (2013.01); *A61B 2018/00577* (2013.01); *A61B 2018/00595* (2013.01); *A61B 2018/00601* (2013.01); *A61B 2018/00875* (2013.01); *A61B 2018/124* (2013.01); *A61B 2018/165* (2013.01)
(58) Field of Classification Search
    CPC ........... A61B 2018/00577; A61B 2018/00595; A61B 2018/00601; A61B 2018/00875; A61B 2018/124; A61B 2018/165; A61B 18/14; A61B 2018/1467
    See application file for complete search history.

(56) References Cited

U.S. PATENT DOCUMENTS

| | | | |
|---|---|---|---|
| 2002/0068931 A1* | 6/2002 | Wong | A61B 18/1206 606/34 |
| 2006/0095032 A1* | 5/2006 | Jackson | A61M 25/10184 606/41 |
| 2007/0062547 A1* | 3/2007 | Pappone | A61B 18/1233 606/41 |
| 2007/0167942 A1* | 7/2007 | Rick | A61B 18/16 606/35 |
| 2007/0244478 A1 | 10/2007 | Bahney | |
| 2008/0021446 A1 | 1/2008 | Swanson | |
| 2008/0125775 A1* | 5/2008 | Morris | A61B 18/1477 606/50 |
| 2008/0281309 A1 | 11/2008 | Dunning et al. | |
| 2008/0281310 A1* | 11/2008 | Dunning | A61B 18/16 607/152 |
| 2009/0036884 A1* | 2/2009 | Gregg | A61B 18/1233 606/35 |
| 2009/0171341 A1 | 7/2009 | Pope et al. | |
| 2009/0171345 A1 | 7/2009 | Miller et al. | |
| 2009/0198229 A1* | 8/2009 | Dunning | A61B 18/16 606/35 |
| 2009/0318905 A1* | 12/2009 | Bhargav | A61B 18/14 606/1 |
| 2012/0089140 A1 | 4/2012 | Dunning et al. | |
| 2013/0304049 A1* | 11/2013 | Behnke, II | A61B 18/1206 606/34 |
| 2014/0228662 A1* | 8/2014 | Park | A61B 5/291 600/372 |
| 2016/0184823 A1* | 6/2016 | Fischer | B01L 3/502707 422/502 |
| 2017/0245912 A1 | 8/2017 | Bhargav et al. | |
| 2018/0085163 A1* | 3/2018 | Zeledon | A61B 34/20 |
| 2021/0204996 A1* | 7/2021 | Ko | A61N 1/06 |

OTHER PUBLICATIONS

Japanese Official Action dated Aug. 15, 2023 from related JP 2019-199670 together with English language translation.
Chinese Official Action dated Aug. 26, 2023 from related CN 201911071819.6 together with English language translation.
European Examination Report dated Apr. 20, 2023 from related EP 19 206 945.8.
Israeli Office Action dated Jul. 31, 2024, received in a corresponding foreign application, namely Israeli Patent Application No. 269631, 4 pages.

* cited by examiner

INDIFFERENT ELECTRODE WITH SELECTABLE AREA

FIELD OF THE INVENTION

The present invention relates generally to medical procedures that involve the passage of electric current through biological tissue, and particularly to tools such as radiofrequency (RF) ablation, cauterization, dissection and/or cutting tools.

BACKGROUND OF THE INVENTION

Various radiofrequency (RF) ablation systems for clinical use were proposed. For example, U.S. Patent Application Publication 2009/0171345 describes a catheter and patch electrode system for use with an RF ablation generator, having a four-wire interface for improved impedance measurement. The four-wire interface includes a pair of source connectors across which an excitation signal is produced and a pair of sense connector wires across which the impedance is measured. The RF ablation generator may also produce an ablation signal across a source wire and an indifferent return patch electrode. The catheter includes a shaft having a distal end, with an ablation tip electrode disposed at the distal end. A source lead is electrically coupled to the tip electrode. An optional sense lead is also electrically coupled to the tip electrode. The system further includes a source return and a sense return electrode (e.g., skin patches), either or none of which may be combined with the indifferent return, and if used may be placed on opposite sides of the patient for improved performance. The impedance sensor circuit produces an excitation signal across the source connectors, which is then carried to the tip electrode, travels through the complex load (tissue volume), and returns to the generator via a patch electrode. The impedance is measured by observing the voltage drop across the sense connectors caused by the excitation signal.

As another example, U.S. Patent Application Publication 2008/0021446 describes an internal indifferent electrode device including a flexible shaft, an energy transmission device adapted to be inserted into the body supported on the shaft, and a connector adapted to mate with the power return connector of a power supply apparatus. An exemplary internal indifferent electrode is provided with eight spaced electrodes that together act like a large single indifferent return electrode, thereby obviating the need for the conventional external patch electrode. The indifferent patch electrodes are connected to a pair of power return connectors of an electrosurgical unit. The multiple electrodes are either all shorted together or shorted together at one of the two return connectors.

SUMMARY OF THE INVENTION

An embodiment of the present invention provides a system including an indifferent electrode, electrical switching circuitry, and a processor. The indifferent electrode, which is configured for placement on a body of a patient, includes multiple electrically-conducting sub-electrodes that are electrically-insulated from one another. The electrical switching circuitry is configured to receive a control signal that specifies a selected subset of the sub-electrodes, and in response to electrically connect the selected subset, so as to close an electrical circuit passing through the body of the patient. The processor is configured to determine a required surface area of the indifferent electrode, select the subset of the sub-electrodes that together have the required surface area, and instruct the electrical switching circuitry to electrically connect the selected subset of the sub-electrodes.

In some embodiments, the processor is configured to determine the required surface area based on an indication from an impedance measurement.

In some embodiments, the processor is configured to determine the required surface area based on an input from a user.

In an embodiment, the processor is configured to automatically adjust the surface area of the indifferent electrode during a catheter-based radiofrequency (RF) ablation procedure.

In another embodiment, the processor is configured to automatically adjust the surface area of the indifferent electrode during a probe-based RF cauterization procedure.

In some embodiments, the sub-electrodes include concentric electrically-conducting rings.

In some embodiments, the sub-electrodes have respective areas that form a binary sequence.

In an embodiment, the control signal includes a binary word in which each bit specifies whether a respective sub-electrode is to be active.

There is additionally provided, in accordance with an embodiment of the present invention, a method, including placing an indifferent electrode on a body of a patient, the indifferent electrode including multiple electrically-conducting sub-electrodes that are electrically-insulated from one another. A required surface area of the indifferent electrode is determined. A subset of the sub-electrodes that together have the required surface area is selected. The selected subset of the sub-electrodes is electrically connected, so as to close an electrical circuit passing through the body of the patient.

The present invention will be more fully understood from the following detailed description of the embodiments thereof, taken together with the drawings in which:

DETAILED DESCRIPTION OF EMBODIMENTS

Overview

Figure 1:
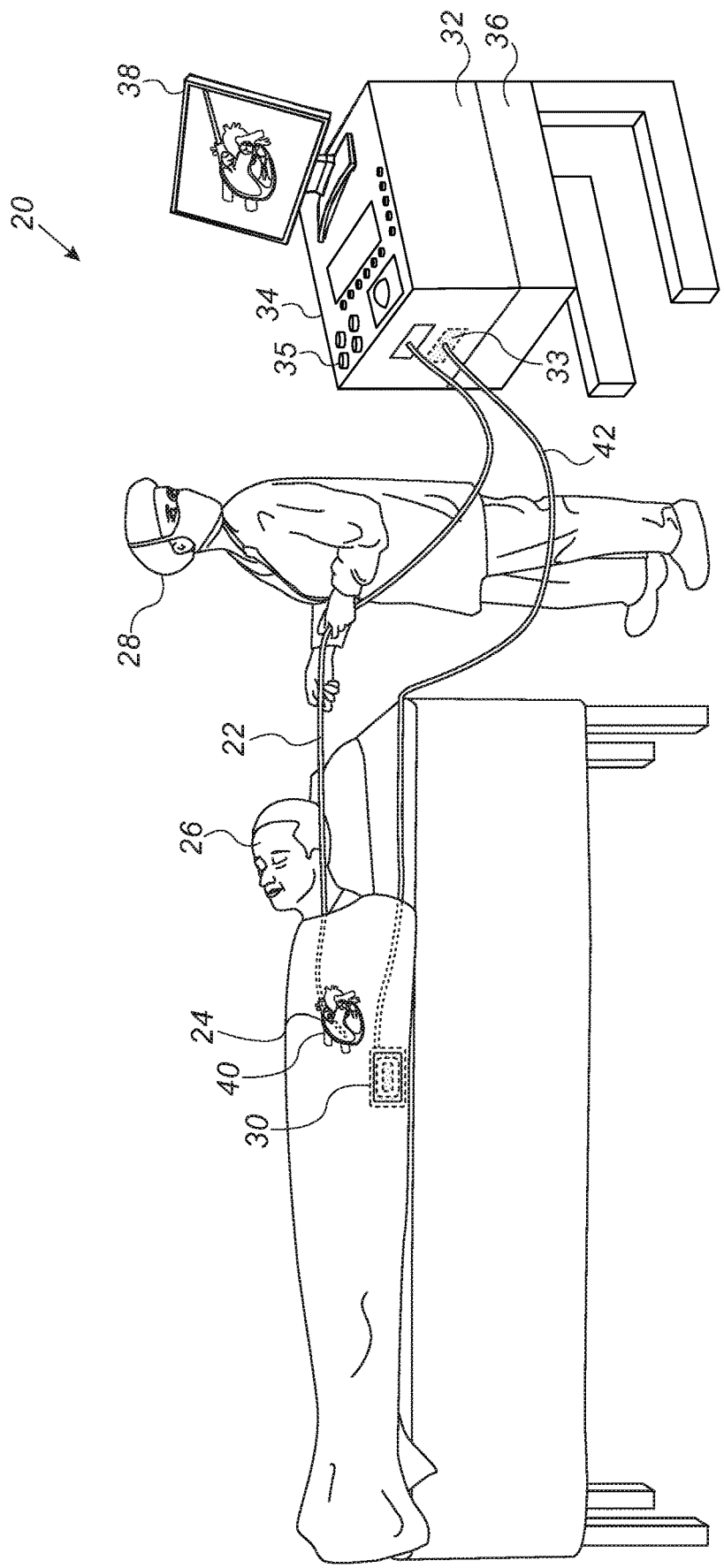
FIG. 1 is a schematic, pictorial illustration of a catheter-based cardiac ablation system comprising an indifferent electrode, in accordance with an embodiment of the present invention.

During radiofrequency (RF) ablative or electrocautery treatments, an accurate amount of electrical energy may be required to dissipate at a given location in an organ of a patient. In a typical catheter-based ablation (e.g., denervation) or invasive cauterization (e.g., sealing a bleeding artery) procedure, a probe comprising an RF ablation or cautery electrode, is inserted into the organ, and the electrode is brought into contact with the given location to be ablated. RF pulses are applied between the electrode and an external return electrode (also referred to as an indifferent electrode) that is attached to the patient's skin.

The amount of RF energy dissipated at the given location depends on the impedance offered by the indifferent electrode. This impedance depends on various factors, including the location on the body of the patient at which the indifferent electrode is attached, patient-to-patient variations, and the active area of the indifferent electrode. Unless accounted for, the electrical impedance of an indifferent electrode may therefore vary over a relatively large range, and this variation may cause undesired clinical side effects relating to how and where exactly (e.g., how deep into tissue) the radiofrequency ablation or cauterization energy is dissipated in the body.

As the impedance offered by the indifferent electrode depends, as noted above, on the place on the body where the electrode is attached, prior to ablations or cauterizations, a physician wanting to control the impedance reading may need to shift the indifferent electrode patch to different locations on the patient's body in an attempt to achieve the desired impedance.

For example, in cardiac ablation procedures the indifferent electrode is usually placed on the torso of the patient, but the electrode may alternatively be placed on a thigh. Such a placement search routine requires additional time, as well as causing a degree of uncertainty, since the physician does not know exactly where to place the patch. If the adhesive is compromised during the process the patch may also require replacement.

Embodiments of the present invention that are described and illustrated hereinafter provide an indifferent electrode with a selectable area, which may be used to achieve more consistent RF ablations or cauterizations. Although the embodiments described herein refer mainly to cardiac RF ablation, the disclosed techniques can be used in various tools and procedures, e.g., for cauterization, dissection and/or cutting. In the present context, the term "cauterization" is meant to refer to dissection, cutting and similar procedures, as well.

In an embodiment, prior to a first ablation or cauterization, a processor of the RF ablation/cauterization system selects the proper amount of surface area of the indifferent electrode to be active (i.e., to be in electrical contact). For example, if the physician places the indifferent electrode directly over the patient's heart, the processor selects a small area to be active. If the physician places the indifferent electrode on the thigh of the patient, the processor selects a large area to be active.

In some embodiments, the disclosed indifferent electrode is divided into multiple electrically conducting plates (also referred to as sub-electrodes) that are electrically insulated from each other. In an embodiment, the processor instructs electrical switching circuitry, included in the RF ablation/cauterization system, to electrically connect one or more of the plates to the RF generator, so as to achieve the required surface area, as determined, for example, by a processor of the RF ablation/cauterization system.

In some embodiments, the processor is configured to estimate the required surface area based on an indication from an impedance measurement. In an embodiment, the impedance is measured between the indifferent electrode and the ablation/cauterization electrode of the catheter/probe. In another embodiment, the multiple isolated sub-electrodes of the indifferent electrode are activated at the beginning of the procedure to standardize a given starting impedance prior to the first ablation/cauterization and prior to the patient receiving significant saline which would change the impedance of the setup.

In some embodiments, the disclosed indifferent electrode is divided into multiple concentric ring-electrodes. Each concentric electrode ring has twice the area of the ring immediately inside it, and the rings are independently wired to an RF ablation/cauterization generator via switching circuitry that is controlled by a processor (i.e., each ring-electrode is independently electrically connectable).

For example, if the area of the smallest electrode is "AR," and the indifferent electrode comprises a total of eight concentric electrode plate-rings as described above, the actual area of the indifferent electrode can thus be selected in a range from 1*AR to 255*AR, by selection of the different rings. In this scheme, eight areas are each wired independently to the RF generator, yielding 255 different surface area values, ranging from 1*AR to 255*AR, with a resolution of 1*AR. By making the surface area of each ring twice that of the electrode immediately inside it, the number of wires connected to the electrode is minimized, while maximizing the range of selectable areas as well as the number of discrete area choices.

The processor is programmed in software containing a particular algorithm that enables the processor to conduct each of the processor-related steps and functions outlined above.

The disclosed indifferent electrode with a selectable area thus enables accurate selection of the impedance of a return electrode (indifferent electrode), which may improve the accuracy and stability, and hence the efficacy and safety, of RF ablative procedures or RF electrocautery procedures, such as cardiac RF ablation or cerebrovascular RF electrocautery procedure, respectively.

System Description

FIG. 1 is a schematic, pictorial illustration of a catheter-based cardiac ablation system comprising an indifferent electrode, in accordance with an embodiment of the present invention. FIG. 1 depicts a physician 28 performing a unipolar ablation procedure on a patient 26, using an ablation catheter 22.

In this procedure, physician 28 first inserts the distal tip 40 of catheter 22 into patient 26, and then navigates distal tip 40 to the tissue that is to be ablated. For example, the physician may advance the distal tip through the vasculature of patient 26 until the distal tip is in contact with tissue located within heart 24 of patient 26.

Next, while distal tip 40 contacts the tissue, the physician causes radiofrequency (RF) electric currents to be passed between one or more electrodes on distal tip 40 and an indifferent (i.e., neutral) electrode patch 30 that is coupled externally to the subject, e.g., to the subject's back.

Before passing RF currents through indifferent electrode patch 30, a processor 36 selects a proper amount of surface area of indifferent electrode patch 30 to be active on the electrode in order to optimize ablation, as further described below.

Typically, catheter 22 is connected to a console 34 comprising controls 35, which are used by the physician to control the parameters of the ablating currents. In particular, in response to the manipulation of controls 35 by physician 28, a processor 36 adjusts the parameters of the ablating currents by outputting appropriate instructions to an RF generator 32 that generates the currents. As seen, indifferent electrode patch 30 is connected to RF generator 32 via an electrical switching circuitry 33 that enables the selection of an area of indifferent electrode 30, as described below, via a cable 42. In some embodiments, system 20 further comprises a display 38, and processor 36 causes display 38 to display relevant output to physician 28 during the procedure.

Notwithstanding the particular type of procedure depicted in FIG. 1, it is noted that the embodiments described herein may be applied to any suitable type of procedure that requires an indifferent electrode with a selectable area, such as, for example, an electrosurgical procedure.

Processor 36 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 36 runs a dedicated algorithm as described herein, including in FIG. 3, that enables processor 36 to perform the disclosed steps.

Indifferent Electrode with Selectable Area

Figure 2:
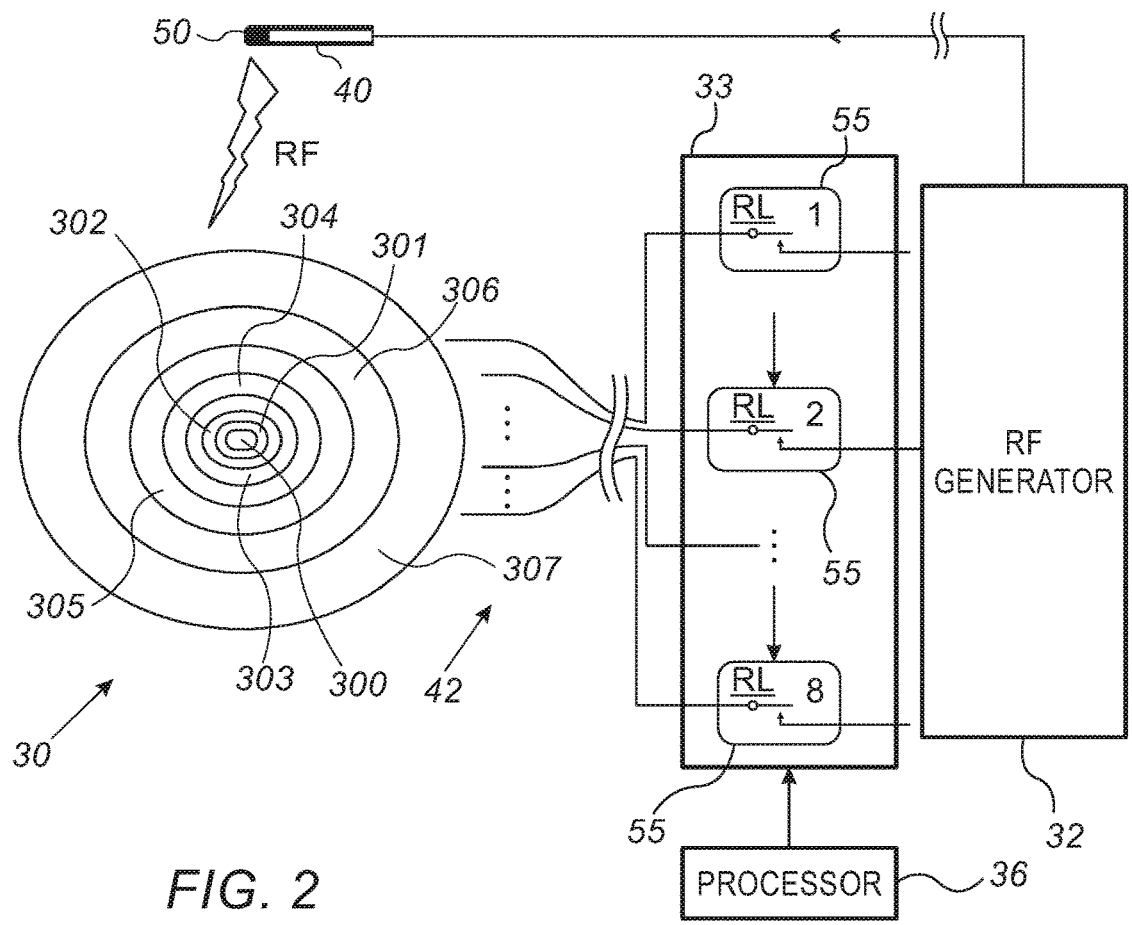
FIG. 2 is a detailed view of elements of the ablation system and the indifferent electrode of FIG. 1, in accordance with an embodiment of the present invention.

FIG. 2 is a detailed view of elements of ablation system 20 and indifferent electrode 30 of FIG. 1, in accordance with an embodiment of the present invention. As seen, RF generator 32 delivers RF current between ablation electrode 50 on distal tip 40 of catheter 22 and return indifferent electrode 30 that is connected via another lead back to RF generator 32. Electrode 30 is connected to RF generator 32 via switching circuitry 33, which comprises relays 55. Individual relays of relay 55 are controlled by processor 36, and an instruction by processor 36 is received in switching circuitry 33 as a control signal. In an embodiment, the electrical switching circuitry receives the control signal from RF generator 32.

In the present example, indifferent electrode 30 comprises eight sub-electrodes 300-307, surrounding one another in a concentric geometry. The area of each sub-electrode is twice the area of the next-inner sub-electrode. In other words, the area of sub-electrode 307 is twice the area of sub-electrode 306, the area of sub-electrode 306 is twice the area of sub-electrode 305, and so on.

Based on a required active area, from 1*AR to 255*AR, where AR is the area of the innermost sub-electrode 300 of indifferent electrode 30, processor 36 directs each of eight relays 55 to connect, or disconnect, one of eight respective rings of indifferent electrode 30 to RF generator 32.

In an embodiment, the desired area can be represented in binary format, i.e., if an area of 170*AR is desired, then 170 in decimal format is converted to binary as 10101010, which directly corresponds to a wiring schematic (e.g., in which outermost ring 307 of area 128*AR is connected, next inner ring 306 of area of 64*AR is disconnected, next inner ring 305 of 32*AR is connected, next inner ring 304 of 16*AR is disconnected, next inner ring 303 of area of 8*AR is connected, next inner ring 302 of 4*AR is disconnected, next inner ring 301 of 2*AR is connected, and innermost area AR 300 disconnected).

The example illustration shown in FIG. 2 is chosen purely for the sake of conceptual clarity. For example, the actual shape of indifferent electrode 30 may be elliptical or even non-concentric, such as a configuration comprising a grid made by interleaving rectangular plate-electrodes. However, the disclosed embodiment, in which each electrode is twice the size of the previous electrode, allows for the greatest number of areas with a uniform step size which requires the fewest connections. As another example, the switching method, using relays, was brought by way of example, whereas other switching devices, may be used, such as, for example switching diodes.

Figure 3:
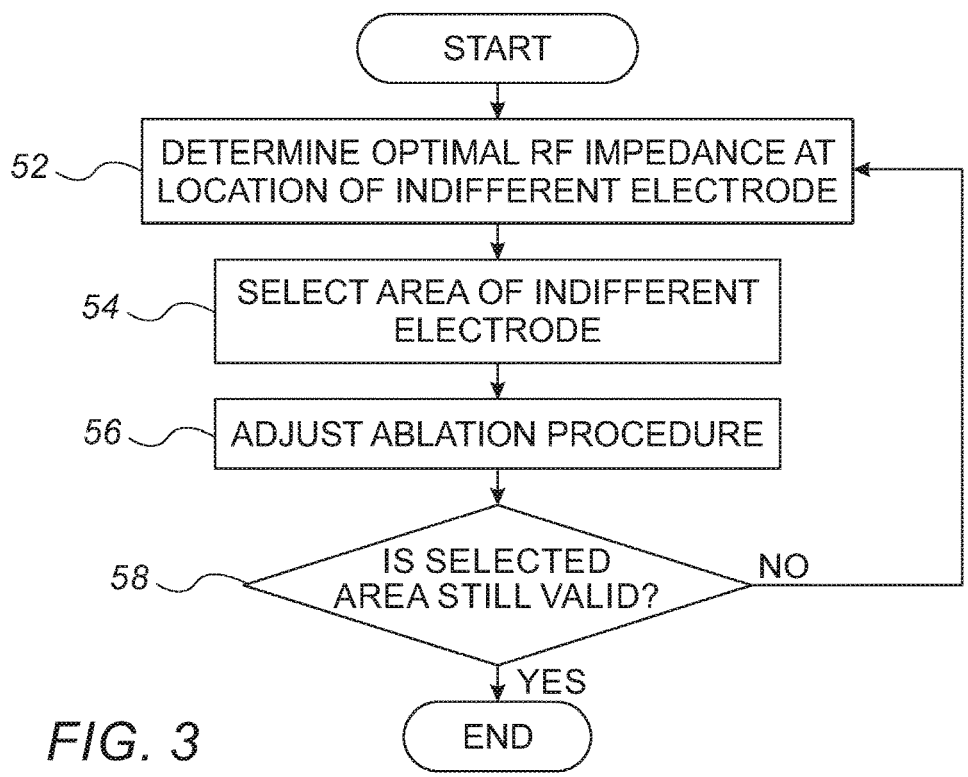
FIG. 3 is a flow chart of an algorithm that schematically illustrates a method for selecting an area of an indifferent electrode, in accordance with an embodiment of the present invention.

FIG. 3 is a flow chart that schematically illustrates a method and algorithm for selecting an area of the indifferent electrode, in accordance with an embodiment of the present invention. The algorithm according to the present embodiment carries out a process that begins with processor 36 determining an optimal RF impedance for the location of indifferent electrode patch 30, at an impedance determination step 52. The optimal impedance is determined, for example, based on an impedance measured between indifferent electrode 30 and electrode 50 of ablation catheter 22. Next, processor 36 selects, using the dedicated algorithm, a proper amount of surface area of indifferent electrode patch 30 to be active, at an electrode-area selection step 54.

Prior to the first ablation, the processor can select the proper amount of surface area to be active on the indifferent electrode, which allows the procedure starting impedance to be more consistent. If the physician places the indifferent electrode directly over the patient's heart, the processor then selects a small area to be active. If the physician places the indifferent electrode on the thigh of the patient, the processor then selects a large area to be active.

Depending upon the generator, the usual allowable starting impedances range between 50Ω and 250Ω. Clinically, the typical values are narrower than the above-mentioned range, but, on average, there is still a >50Ω difference between hospital sites, based upon where the lab applies the indifferent electrode on the patient. From patient to patient there may also be some variability due to body size, blood conductivity, skin conductivity, etc.

Once the catheter is in the heart, the processor selects the desired indifferent electrode starting impedance for the procedure through various combinations of areas of the patch. This could be done, for example, immediately prior to the first ablation. In an embodiment, the generator connects a given area value AR, measures the impedance, then connects area value 255*AR and re-measures the impedance. A linear interpolation between the values provides a good prediction for the next area to try, for example, 133*AR. After a new linear interpolation between 133*AR of the two extremes, an additional prediction for a new value to try is provided. Within a couple of attempts, the processor should be able to determine the best choice among the available 255 options, thus reducing the variability in starting impedance.

In an embodiment, processor 36 reselects the patch area during the procedure. For example, the generator may attempt to normalize impedance before each ablation. While optimizing patch impedance, the catheter floats in blood to give a more consistent measurement, otherwise, if the catheter is touching tissue, then the type of tissue it was touching and how much surface area was in contact could vary the measured impedance.

Next, physician 28 starts a cardiac ablation treatment of patient 26 that includes adjustments, such as to the contact location of the catheter inside heart 24. The adjustments change the initial electrical setting based on which indifferent electrode area was initially selected at step 52. Processor 36 monitors the electrical setting, for example, by receiving impedance readings, at a selected area validation step 56. If the selected area is invalid then the selection process repeats by returning to step 52. If the selected area is valid then the ablation process continues without adjustment of indifferent electrode 30 area, and so on, until ablation treatment ends.

The example flow chart shown in FIG. 3 is chosen purely for the sake of conceptual clarity. The present embodiment also comprises additional steps of the algorithm, such as applying irrigation, which have been omitted from the disclosure herein purposely on order to provide a more simplified flow chart.

Although the embodiments described herein mainly address cardiac applications, the methods and systems described herein can also be used in other applications, such as in neurology, otolaryngology, nephrology, and general surgery utilizing RF ablation or cauterization tools.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
an indifferent electrode, which is configured for placement at a first location on a body of a patient, the indifferent electrode comprising multiple electrically-conducting sub-electrodes that are electrically-insulated from one another;
electrical switching circuitry, configured to receive a control signal that specifies a selected subset of the sub-electrodes, and, in response to the control signal, to electrically connect the selected subset, so as to close an electrical circuit with an RF electrode in contact with tissue within the body of the patient at a second location to receive electrical energy from the RF electrode; and
a processor, which is configured to:
determine a first RF impedance based on impedance measurements between the indifferent electrode positioned at the first location and the RF electrode positioned at the second location;
select a surface area of the indifferent electrode to be active based on the first RF impedance;
select a subset of the sub-electrodes that together have the surface area resulting in the first RF impedance based impedance measurements from a plurality of combinations of the sub-electrodes;
instruct the electrical switching circuitry to electrically connect the selected subset of the sub-electrodes to perform a procedure using the RF electrode;
monitoring the RF procedure to determine a change in position of the RF electrode to a third location;
determine a second RF impedance based on impedance measurements between the indifferent electrode positioned at the first location and the RF electrode at the changed position of the third location;
if the selected subset of the sub-electrodes is determined to result in the second RF impedance being outside of a target impedance range, automatically reselect a subset of electrodes from the plurality of combinations of the sub-electrodes to adjust the surface area of the indifferent electrode such that the second RF impedance is maintained within the target impedance range; and
if the selected subset of the sub-electrodes is determined to result in the second RF impedance being within the target impedance range, continue using the selected subset of the sub-electrodes.

2. The system according to claim 1, wherein the procedure using the RF electrode is a catheter-based radiofrequency (RF) ablation procedure.

3. The system according to claim 1, wherein the procedure using the RF electrode is a probe-based RF cauterization procedure.

4. The system according to claim 1, wherein the sub-electrodes comprise concentric electrically-conducting rings.

5. The system according to claim 1, wherein the control signal comprises a binary word in which each bit specifies whether a respective sub-electrode is to be active.

6. A method comprising:
placing an indifferent electrode at a first location on a body of a patient, the indifferent electrode comprising multiple electrically-conducting sub-electrodes that are electrically- insulated from one another;
determining a first RF impedance based on impedance measurements between the indifferent electrode positioned at the first location and an RF electrode positioned at a second location;
selecting a surface area of the indifferent electrode to be active based on the first RF impedance;
selecting a subset of the sub-electrodes that together have the surface area resulting in the first RF impedance based impedance measurements from a plurality of combinations of the sub-electrodes;
electrically connecting the selected subset of the sub-electrodes, so as to close an electrical circuit with the RF electrode in contact with tissue within the body of the patient at the first location to receive electrical energy from the RF electrode to perform a procedure using the RF electrode;
monitoring the RF procedure to determine a change in position of the RF electrode to a third location;
determining a second RF impedance based on impedance measurements between the indifferent electrode positioned at the first location and the RF electrode at the changed position of the second location;
if the selected subset of the sub-electrodes is determined to result in the second RF impedance being outside of a target impedance range, automatically reselecting a subset of electrodes from the plurality of combinations of the sub-electrodes for adjusting the surface area of the indifferent electrode such that the second RF impedance is maintained within the target impedance range; and
if the selected subset of the sub-electrodes is determined to result in the second RF impedance being within the target impedance range, continue using the selected subset of the sub-electrodes.

7. The method according to claim 6, wherein the procedure using the RF electrode is a catheter-based radiofrequency (RF) ablation procedure.

8. The method according to claim 6, wherein the procedure using the RF electrode is a probe-based RF cauterization procedure.

9. The method according to claim 6, wherein the sub-electrodes comprise concentric electrically-conducting rings.

10. The method according to claim 6, wherein receiving the control signal comprises receiving a binary word in which each bit specifies whether a respective sub-electrode is to be active.

11. The system according to claim 1, wherein the target impedance range is from about 50Ω to about 250Ω.

* * * * *